United States Patent [19]
Shinitzky

[11] Patent Number: 6,008,001
[45] Date of Patent: Dec. 28, 1999

[54] DIAGNOSIS OF THE SUSCEPTIBILITY OF CONTRACTING SCHIZOPHRENIA

[75] Inventor: Meir Shinitzky, Kfar Shmaryahu, Israel

[73] Assignee: Yeda Research and Development Co. Ltd., Rehovot, Israel

[21] Appl. No.: 08/637,786

[22] PCT Filed: Oct. 27, 1994

[86] PCT No.: PCT/US94/12228

§ 371 Date: May 6, 1996

§ 102(e) Date: May 6, 1996

[87] PCT Pub. No.: WO95/12685

PCT Pub. Date: May 11, 1995

[30] Foreign Application Priority Data

Nov. 5, 1993 [IL] Israel ........................................ 107515

[51] Int. Cl.$^6$ .................................................. G01N 33/53
[52] U.S. Cl. .................... 435/7.2; 435/7.21; 435/7.92; 436/503; 436/518; 436/811
[58] Field of Search ........................... 435/7.1, 7.2, 7.21, 435/7.24, 7.9, 7.92, 7.95, 975, 503, 506; 436/518, 519, 63, 811

[56] References Cited

U.S. PATENT DOCUMENTS 4,717,654  1/1988  Savoca .

OTHER PUBLICATIONS

T. J. Crow, "Molecular Pathology of Schizophrenia: More Than One Disease Process?", *British Medical Journal*, vol. 280, pp. 66–68, Jan. 12, 1980.

Peter F. Liddle, "The Symptoms of Chronic Schizophrenia. A Re–examination of the Positive–Negative Dichotomy", *British Journal of Psychiatry*, vol. 151, pp. 145–151, 1987.

Lynn E. Delisi, M.D. et al., "Is Schizophrenia a Viral or Immunologic Disorder?", *Psychiatric Clinics of North America*, vol. 9, No. 1, pp. 115–132, Mar. 1986.

Lynn E. Delisi et al., "Are There Antibodies Against Brain in Sera from Schizophrenic Patients? Review and Prospectus", *Biol. Psychiatry*, vol. 20, 110–115, 1985.

H. H. Fudenberg et al., "Is Schizophrenia an Immunologic Receptor Disorder?", *Medical Hypotheses*, vol. 12, pp. 85–93, 1983.

Branislav D. Jankovic, "From Immunoneurology to Immunopsychiatry: Neuromodulating Activity of Anti–Brain Antibodies", *International Review of Neurobiology*, vol. 26, pp. 249–314, 1985.

Meir Shinitzky et al., "Platelet Autoantibodies in Dementia and Schizophrenia Possible Implication for Mental Disorders", *Annals New York Academy of Sciences*, vol. 621, pp. 205–217.

Michel Leporrier et al., "Detection and Quantification of Platelet–bound Antibodies with Immunoperoxidase", *British Journal of Haematology*, vol. 42, pp. 605–611, 1979.

Brian R. Clark et al., "Enzyme–Linked immunosorbent Assay (ELISA): Theoretical and Practical Aspects", *Enzyme–Immunoassay*, published 1980 by CRC Press, Inc. (Boca Raton, FL), pp. 167–179.

Alister Voller et al., "Enzyme–Linked Immunosorbent Assay", *Manual of Clinical Laboratory Immunology*, published 1989 by American Society for Microbiology (Washington, D.C.), pp. 99–109.

Tanning, Tissue Antigens, 25:19–27, 1985.

Leporrer et al, British Journal of Haematology, 42:605–611, 1979.

Shinitzky et al, Annals New York Academy of Scunces, 621:205–217, 1991.

Harlow et al, Antobodies: A Laboratory Manual, Cold Spring Harbor Press, NY 1988, pp. 205–217, 234–237 and 560–566 and 626–631.

*Primary Examiner*—Patricia A. Duffy
*Attorney, Agent, or Firm*—Oliff & Berridge, PLC

[57] ABSTRACT

There is described an assay for the diagnosis of a mental disorder in an individual. A blood sample, a platelet-containing fraction thereof, or a fraction containing platelet-associated antibodies (PAA) shed from the platelets is withdrawn from the individual to be diagnosed. The withdrawn sample is contacted with an anti-human immunoglobulin antibody lacking the Fc domain (Fc-less anti-hIg antibody) and the degree of binding thereof to the PAA is determined. A degree of binding above that found in normal individuals indicates that diagnosed individual has a high likelihood of having a mental disorder.

8 Claims, 2 Drawing Sheets

DIAGNOSIS OF THE SUSCEPTIBILITY OF CONTRACTING SCHIZOPHRENIA

FIELD OF THE INVENTION

The present invention is generally in the field of diagnostic assays. More specifically, the present invention provides an assay for the diagnosis of mental disorders, particularly schizophrenia.

PRIOR ART

The following is a list of prior publications referred to in the present specification:
1. Crow, T. J., 1980. Molecular pathology of schizophrenia: More than one disease process? Br. Med. J., 280:66–68.
2. Klein, D. F., Gittelman, R., Quitkin, F. and Rifkin, F., 1980. Diagnosis and Drug Treatment of Psychiatric Disorders: Adults and Children. Williams and Wilkins, Baltimore.
3. Liddle, P. F., 1987. The symptoms of chronic schizophrenia. A re-examination of the positive-negative dichotomy, Br. J. Psychiatr., 151:145–151.
4. DeLisi, L. E. and Crow., T. J., 1986. Is schizophrenia a viral or immunological disorder? Psychiatr. Clin. North. Am., 9:115–132.
5. DeLisi, L. E., R. J., Weber and C. B., Pert. 1985. Are there antibodies against brain in sera from schizophrenic patients? Review and Perspectus. Biol. Psychiatry, 20:94–119.
6. Fudenberg, H. H., Whitten, H. D., Merler, E and Farmati, O., 1983. Is schizophrenia an autoimmunologic receptor disorder? Med. Hypothes. 12:85–93.
7. Jankovic, B. D., 1984. From Immunoneurology to immunopsychiatry. Neuromodulating activity of antibrain antibodies. Int. Rev. Neurobiol., 26:249–314.
8. Shinitzky, M., Deckman, M., Kessler, A., Sirota, P., Rabbs, A. and Elizur., A, 1991. Platelet autoantibodies in dementia and schizophrenia—possible implication for mental disorders, An. N.Y Acad. Sc. 621:205–217.
9. Leporrier, M., Dighiero, G., Auzemery, M. and Binet, J. L., 1979. Detection and quantification of platelet-bound antibodies with immunoperoxidase, Br. J. Haematol, 42:605–611.

The acknowledgement herein of the above art, should not be construed as an indication that this art is in any way relevant to the patentability of the invention as defined in the appended claims.

The above publications will be acknowledged in the following by indicating their number from the above list:

BACKGROUND OF THE INVENTION

It is becoming clear today that mental disorders are a scientific reflection of the biological abnormalities in the brain. However, notwithstanding the growing understanding of brain anatomy and function, which allows at time a post-mortem diagnosis of a mental disorder, for most mental disorders there are no available objective assays which will allow their diagnosis in living individuals. Psychiatrists or neurologists when attempting to diagnose a mental disorder, have to rely on a series of tests, which very often cannot be interpreted unequivocally. Such a test series is generally a tedious process and there are thus no effective means available today to a practitioner, for a large scale screening of mental disorders.

Schizophrenia is one of the most severe and prevalent mental disorders. Due to its varied symptomatology and to its complex etiology, it is still debatable whether schizophrenia represents a distinct mental disorder, or several different mental diseases grouped under a common name.

A correlation between the occurrence of schizophrenia and the occurrence of various physiological phenomena has been found, but the relevancy of these phenomena to the disease's etiology is still debatable[1–3]. Despite lack of consistent experimental evidence, hypotheses concerning the involvement of autoimmune elements in schizophrenia have been suggested[4–7]. However, positive indication to the presence of autoantibodies in schizophrenic patients were obtained only in about 25% of tested patients[4,5].

The existence of elevated levels of autoantibodies on blood platelets of both schizophrenic and demented patients has been reported recently[8]. In that study, the level of autoantibodies present on the surfaces of blood platelets (termed hereinafter "platelet associated antibodies" (PAA)) isolated from schizophrenic patients, patients with other effective mental disorders, dementia patients, (both treated with neuroleptics and untreated) and normal control subjects was determined by the use of anti-human IgA, IgE, IgG and IgM antibodies. The results of this study demonstrated that schizophrenic patients and demented patients had on the average about twice the level of PAA as compared to age-matched normal controls. Notwithstanding this statistically significant difference in the level of PAA between schizophrenic and demented patients versus normal controls, the difference was too small to serve as a basis for diagnosis of schizophrenia or dementia, or for screening populations for these mental disorders owing to the high proportion of both false positive and false negative results.

SUMMARY OF THE INVENTION

In accordance with the present invention, it was surprisingly found that by the use of an anti-human immunoglobulin antibody (an antibody directed against a human immunoglobulin; hereinafter: "anti-hIg antibody") lacking the Fc domain (hereinafter: "Fc-less anti-hIg antibody") instead of a whole anti-hIg antibody as in the aforementioned Shinitzky et al. reference[8], the detected difference in the average levels of PAA between schizophrenic and normal individuals becomes much more significant. Furthermore, by the use of a Fc-less anti-hIg antibody, the proportion of false positive results is reduced dramatically. Thus, the use of Fc-less anti-hIg antibodies opens the way for a sensitive assay for the diagnosis and screening of various mental disorders such as schizophrenia.

The present invention provides an assay for the diagnosis of mental disorder in an individual, comprising:
(a) obtaining a sample from said individual, being a blood sample, a platelet-containing fraction thereof, or a fraction containing platelet-associated antibodies (PAA) shed from the platelets;
(b) contacting said sample with anti-human immunoglobulin antibody lacking the Fc domain (Fc-less anti-hIg antibody); and
(c) determining the degree of binding of said antibodies to the PAA in said sample, a degree of binding above that found in normal individuals indicating that said individual has a high likelihood of having a mental disorder.

The diagnosed mental disorders may, for example, be schizophrenia or dementia.

The platelet-containing fraction is typically a platelet rich plasma (PRP), which can be prepared by methods generally known per se.

The Fc-less anti-hIg antibody is typically a Fc-less anti-hIgG antibody (i.e. a single domain antibody directed against human IgG).

The Fc-less antibody may be an Fab or an F(ab')$_2$ fragment of an anti-hIg antibody or a part thereof which contains the fragments' binding domain; a single chain antibody; and the like.

The degree of binding of said Fc-less anti-hIg antibody to the platelets can be determined in a number of ways. By one embodiment of the invention this is determined by the use of a marker conjugated to said Fc-less antibody. Such a marker may, for example, be a radioactive group, a fluorescent group, an enzyme that can catalyze a reaction yielding a detectable product such as horseradish peroxidase (HRP) or alkaline phosphatase, etc.

By another embodiment the degree of binding is determined by the use of a second antibody directed against said single domain antibody, which second antibody is bound to a detachable marker.

By a further embodiment, Fc-less anti-hIg antibodies are immobilized on a support, e.g. onto the walls of a dish, onto beads contained in a column, etc., and the binding level is then determined by passing the PRP through the vessel containing the immobilized antibodies and then measuring the level of the immobilized platelets.

By a still further embodiment, a solid support having immobilized thereon a PAA target antigen, i.e. the antigen to which the PAA are directed, is used. In accordance with a first modification of this embodiment, the platelets are contacted with the support and following an incubation period, the immobilized platelets are treated to shed their PAA, washed away and then the support is reacted the with Fc-less anti-hIg antibodies, which are preferably labelled and the number of bound PAA can thus be determined. By a second modification of this embodiment, the platelets are first treated to shed their PAA, the PAA containing fraction is then reacted with the support and following incubation and washing, the supports are reacted with the Fc-less anti-hIg antibodies which are preferably labelled, and the number of bound PAA is thus determined.

The present invention also provides a kit useful in the above assay. The kit of the invention comprises an anti-hIg antibody lacking the Fc domain. According to one embodiment, the antibodies in the kit are conjugated to a detectable marker. In accordance with another embodiment, the kit comprises also a second type of antibodies directed against the Fc-less antibodies, which second type of antibodies are in turn conjugated to a detectable marker. In accordance with a further embodiment, the antibodies are immobilized onto a support and the kit comprises such a support. In accordance with yet another embodiment an antigen reactive with the PAA is immobilized onto the support and the kit comprises such a support. The kit according to all above embodiments may also comprise the various reagents required for carrying out the assay.

The invention will now be illustrated in the following non-limiting description of a specific embodiment and accompanying drawings.

DESCRIPTION OF A SPECIFIC EMBODIMENT

Patients and control subjects

Figure 1:
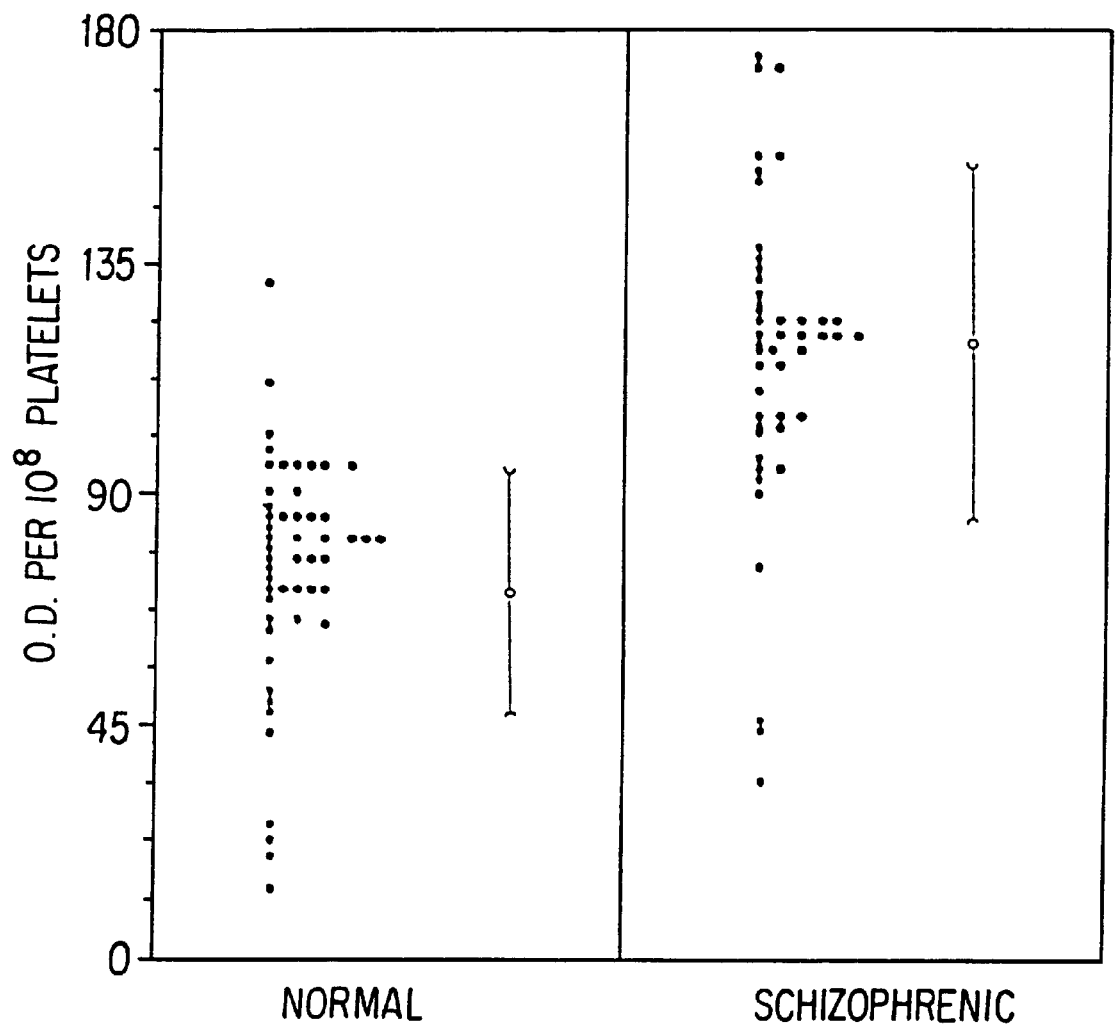
FIG. 1: level of PAA in units of O.D. (optical density) per $10^8$ platelets, obtained from control subjects (A) and schizophrenic patients (B) as determined by HRP labelled rabbit anti-human IgG.

Schizophrenic patients, hospitalized in mental hospitals in Israel participated in this study. They consisted both of patients treated with various neuroleptics and newly diagnosed and untreated patients. All patients were free of any immunological or allergic disorder and their blood biochemistry profile was in the normal range. The control group consisted of healthy volunteers who had no history of psychiatric disorder or any chronic disease.

Determination of PAA levels

Venous blood (20 ml) was drawn before breakfast using sodium citrate solution (sodium citrate—2.2%, citric acid—0.73% dextrose monohydrate—2.45%) as an anticoagulant. Platelet rich plasma (PRP) was obtained by slow centrifugation (100× g for 20 min) at room temperature, and platelets were scored microscopically.

PAA levels were determined either with rabbit anti-human IgG antibodies linked to HRP (as in Shinitzky et al., 1991) or with a Fab fragment of this antibody (inventive assay). Enzyme-linked immunoassay (ELI) based on a color development after binding of the antibody or Fab fragment thereof, was used.

For the ELI procedure (Leporrier et al. Br. J. Haematol., 42, 605 (1979)) 300 µl PRP were centrifuged, the pellet was resuspended in 1 ml of phosphate buffered saline pH 7.2 (PBS). This step was repeated 3 times. The pellet was then resuspended in 0.15 ml PBS containing either rabbit anti-human IgG linked to HRP or its Fab fragment linked to HRP, and incubated for 30 min. at 37° C. After 4 washings with PBS at 4° C., the platelet suspension was incubated with freshly prepared substrate reagent (19.8 ml PBS+0.2 ml methanol containing 2 mg ortho-phenylenediamine++3 µl $H_2O_2$ 30%) for 1 hr at 37° C. The reaction was determined by adding 0.1 ml of 6N sulfuric acid and the O.D. was read at 480 nm. After background subtraction, the O.D. was calculated for $10^8$ platelets per ml (Shinitzky et al., 1991 supra).

Preparation of Fab fragments of rabbit anti-human IgG bound to horseradish peroxidase Activated plastic beads (Immunotip, U.S.A. Scientific Plastics) were coupled with papain as follows: 1 mg papain (Worthington, U.S.A. was mixed in 1 ml of 0.2M sodium cyanoborohydride (Fluka, U.S.A., and was incubated with a single plastic bead for 5–10 minutes, and then washed extensively with PBS. Horseradish peroxidase conjugated rabbit anti-human IgG (BioMakor, Israel; 740 µg in 40 µl), was incubated with gentle shaking with the papain conjugated bead for 5 hours at 37° C. and then passed through a protein A column (Pierce). The Fab fragment of the treated antibodies were collected while washing with 15 ml 10 mM Tris buffer, pH=7.4.

Results

FIG. 1 shows PAA levels in relative units of O.D. of schizophrenic patients (n=43) and of healthy control subjects (n=52) assayed in quadruplicates using HRP labelled rabbit anti-human IgG. The average mean O.D+S.E. obtained for normal and schizophrenic patients was 0.65±0.22 and 1.23±0.35, respectively. As can be seen in FIG. 1, while the results show an average 2 fold increase in the reading in schizophrenic patients versus normal subjects, the individual results show a very high degree of overlap between the two groups which means a high incidence of false positive and false negative results. The assay performed in this manner has thus practically no real diagnostic value.

Figure 2:
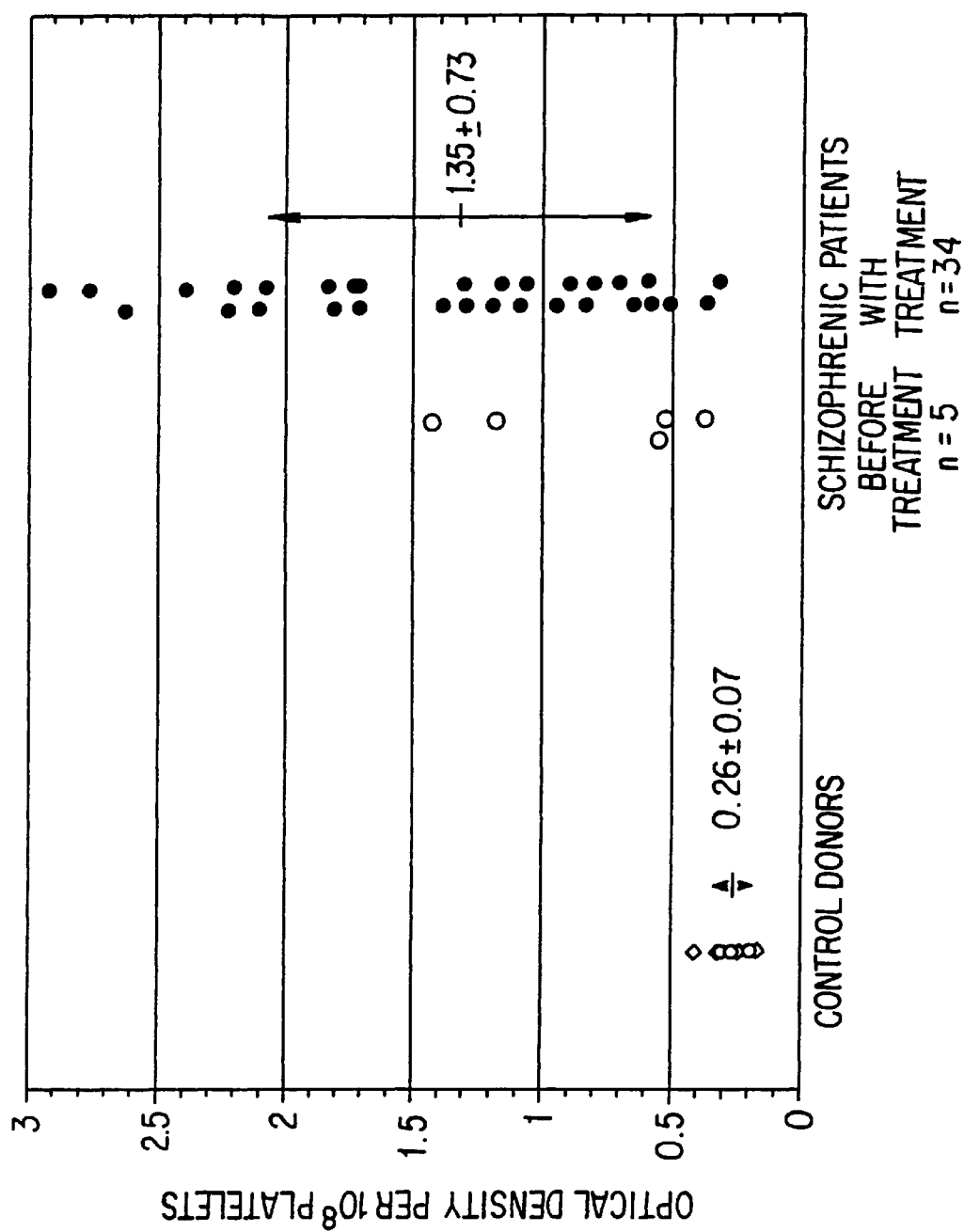
FIG. 2: level of PAA in units of O.D. per $10^8$ platelets, obtained from control subjects (A) and schizophrenic patients (B) (before and after treatment with neuroleptics) as determined by horseradish peroxidase labelled rabbit Fab fragment of anti-human IgG.

FIG. 2 shows PAA levels in relative units of O.D., assayed in quadruplicates obtained for normal subjects control (n=10) and schizophrenic patients both treated with neuroleptics (n=34) and untreated (n=5) determined by HRP labelled Fab fragments of anti-human IgG. The average (mean O.D.+S.E.) obtained for normal and schizophrenic subjects was 0.26±0.07 and 1.35±0.73, respectively.

The ratio between the results obtained with schizophrenic patients and normal subjects while using the Fab fragment is much higher than that obtained by the use of whole antibodies. Furthermore, and even more important, there is very little overlap between the readings from the two groups. Given the results in FIG. 2, it can be seen that if an upper limit for control subjects would have been set, for example, at 0.5 O.D., the assay would have very little false negative or not even one false positive.

I claim:

1. An assay for screening an individual for having susceptibility of having schizophrenia, comprising:

(a) obtaining a sample from said individual, said sample being a platelet-associated antibody (PAA) fraction shed from isolated platelets;

(b) contacting said sample with anti-human immunoglobulin antibody lacking a Fc domain (Fc-less anti hIg antibody); and (c) determining the quantity of binding of the Fc-less anti-hIg antibody to PAA, wherein said quantity of binding above that found in normal individuals indicates that said individual is susceptible of having said schizophrenia.

2. An assay according to claim 1, wherein said Fc-less anti-hIg antibody is a Fc-less anti-hIgG antibody.

3. An assay according to claim 1, wherein said Fc-less anti-hIg antibody is a Fab fragment of an anti-hIg antibody.

4. An assay according to claim 1, wherein said Fc-less anti-hIg antibody is a F(ab')$_2$ fragment of an anti-hIg antibody.

5. An assay according to 1, wherein the anti-hIg antibody is conjugated to a marker.

6. An assay according to claim 5, wherein said marker is an enzyme capable of catalyzing a reaction which yields a detectable product.

7. An assay according to claim 1, wherein the quantity of binding is determined by the use of a second antibody directed against said Fc-less anti-hIg, which second antibody is bound to a detectable marker.

8. An assay according to claim 1, wherein said anti-human immunoglobulin antibody lacking a Fc domain are immobilized on a support.

* * * * *